United States Patent
Lee

[11] Patent Number: 5,876,439
[45] Date of Patent: Mar. 2, 1999

[54] METHOD AND APPARTUS FOR ADJUSTING CORNEAL CURVATURE USING A FLUID-FILLED CORNEAL RING

[75] Inventor: Joseph Y. Lee, Loma Linda, Calif.

[73] Assignee: MicoOptix, LLC, Loma Linda, Calif.

[21] Appl. No.: 856,650

[22] Filed: May 15, 1997

Related U.S. Application Data

[63] Continuation-in-part of Ser. No. 761,362, Dec. 9, 1996, Pat. No. 5,733,334.

[51] Int. Cl.$^6$ ............................................ A61F 2/14
[52] U.S. Cl. ................................. 623/5; 606/166
[58] Field of Search ................ 623/5; 606/107, 606/166, 167

[56] References Cited

U.S. PATENT DOCUMENTS

| | | | |
|---|---|---|---|
| 4,298,004 | 11/1981 | Schachar et al. | |
| 4,452,235 | 6/1984 | Reynolds | |
| 4,607,617 | 8/1986 | Choyce | |
| 4,624,669 | 11/1986 | Grendahl | 623/5 |
| 4,655,774 | 4/1987 | Choyce | 623/5 |
| 4,688,570 | 8/1987 | Kramer et al. | |
| 4,815,463 | 3/1989 | Hanna | |
| 4,834,750 | 5/1989 | Gupta | 623/6 |
| 4,941,093 | 7/1990 | Marshall et al. | 364/413.01 |
| 4,961,744 | 10/1990 | Kilmer et al. | 606/166 |
| 4,976,719 | 12/1990 | Siepser | 606/151 |
| 5,090,955 | 2/1992 | Simon | 606/166 X |
| 5,123,921 | 6/1992 | Werblin et al. | 623/5 |
| 5,188,125 | 2/1993 | Kilmer et al. | 128/898 |
| 5,236,970 | 8/1993 | Christ et al. | 523/113 |
| 5,300,118 | 4/1994 | Silvestrini et al. | 623/5 |
| 5,312,442 | 5/1994 | Kilmer et al. | 606/151 |
| 5,318,047 | 6/1994 | Davenport et al. | 128/898 |
| 5,331,073 | 7/1994 | Weinschenk, III et al. | 526/264 |
| 5,391,201 | 2/1995 | Barrett et al. | 623/5 |
| 5,405,384 | 4/1995 | Silvestrini | 623/5 |
| 5,466,260 | 11/1995 | Silvestrini et al. | 623/5 |
| 5,480,950 | 1/1996 | Wang et al. | 526/258 |
| 5,505,722 | 4/1996 | Kilmer et al. | 606/1 |
| 5,547,468 | 8/1996 | Simon et al. | 623/5 X |

FOREIGN PATENT DOCUMENTS

| 388746 | 7/1973 | Russian Federation . |
|---|---|---|

OTHER PUBLICATIONS

"*Refractive Surgery*," by Dimitri T. Azar, M.D., pp. 1–2, Corneal Biomechanics in Refractive Surgery, by Jesper O. Hjortdal, Chap. 15, pp. 197–208, *The Intrastromal Corneal Ring for the Correction of Myopia*, by Steven M. Verify & David J. Schanzlin, Chap. 27, pp. 365–372, Intracorneal Alloplastic Inclusions, by Johnny M. Khoury, et al., Chap. 28, pp. 373–384, Appleton & Lange, Stamford, Connecticut. Copyright 1997.

(List continued on next page.)

*Primary Examiner*—Mary Beth Jones
*Attorney, Agent, or Firm*—McCutchen, Doyle, Brown & Enersen, LLP

[57] ABSTRACT

An adjustable intrastromal device adapted for implantation in the cornea and formed of a flexible hollow shell composed of a material such as a silicone or urethane polymer, with a chamber that may be filled with a biocompatible material such as saline or gel. Preferably, the device has more than one compartment, each of which is water-tight and distinct from the other compartments. Each compartment contains a predetermined amount of the biocompatible fluid described, and the device is implanted in the cornea in surrounding relation to the optical zone of the cornea. Increased volume displaced by the ring results in greater flattening of the central anterior corneal curvature thus correcting myopia. Preferably, the myopia is slightly overcorrected resulting in more flattening of the cornea than necessary for optimal vision. The corneal curvature is then adjusted after implantation of the device into the cornea by selectively removing the fluid from a specific compartment, thus decreasing the volume of the implant in a discrete fashion and resulting in steepening the corneal curvature and producing a myopic shift.

23 Claims, 13 Drawing Sheets

OTHER PUBLICATIONS

"Principles and Practice of Refractive Surgery," by Richard Elander, M.D., et al.,pp. 1–3, Alloplastic Materials in Lamellar Surgery, by Bernard E. McCarey, pp. 261–276, Synthetic Epikeratoplasty, by Keith P. Thompson, et al., Chap. 39, pp. 405–413, Intrastromal Corneal by David J. Schanzlin, et al., Chap. 40, pp. 415–419, W. B. Saunders Company, Philadelphia, Pennsylvania. Copyright 1997.

Abstract entitled: "Results of a 2–year animal experiment with reticulated polyethylene oxide intrastromal rings," by F. Kuhne, et al., Journal of Fr. Ophthalmology, vol. 17, 1994.2.

Abstract entitled: "Refractive Modeling of the Corneal by Intrastromal Rings," Gabriel Simon, et al., Association of Research in Vision and Ophthalmology, Annula Spring Meeting, Sarsota, Florida, Apr. 30–May 5, 1989, p. 187.

"Effects of Intrastromal Corneal Ring Size and Thickness on Corneal Flattening in Human Eye" by Terry E. Burris, et al., Refractive & Corneal Surgery, vol. 7 Jan./Feb. 1991, pp. 46–50.

"Hydration Stability of Intracorneal Hydrogel Implants," by W. Houdijin Beekhuis, et al., Investigative Ophthalmology & Visual Science/Nov. 1985, vol. 26, pp. 1634–1636.

"Complications of hydrogel Intracorneal Lenses in Monkeys," by W. Houdijin Beekhulis, MD, et al., Arch Ophthalmol, vol. 105, Jan. 1987, pp. 116–122.

"Hydrogel keratophakia: a microkeratome dissection in the monkey model," by W. Houdijn Beekhuis, et al., British Journal of Ophthalmology, 1986, 70, 192–198.

"The Intrastromal Corneal Ring: Two Caes in Rabbits," by Joseph F. Fleming, MD., et al., Journal of Refractive Surgery, Nov./Dec. 1987; vol. 3, No. 6. pp. 227–232.

"Effect of Diameter and Depth on the Response to Solid Polysulfone Intracorneal Lenses in Cats," by Harold Climenhaga MD., et al., Arch Ophthalmo, vol. 106, Jun. 1988, pp. 818–824.

"Flattening of central corneal curvature with Intrastromal Corneal Rings of increasing thickness: An eye–bank eye study," by Terry E. Burris, et al., J. Cataract Refractive Surgery, vol. 19, Supplement 1993, pp. 182–187.

"Refractive Keratoplasty in Monkeys Using Intracorneal Lenses of Various Refractive Lenses," by Bernard E. McCarey, PhD, et al., Arch Ophthalmol, vol. 105, Jan. 1987 pp. 123–126.

Refractive keratoplasty with intrastromal hydrogel lenticular implants, by Bernard E. McCarey, et al., Investigative Opthalmology Visual Science, Jul. 1981, vol. 21, No. 1, Part 1, pp. 107–115. Copyright 1981.

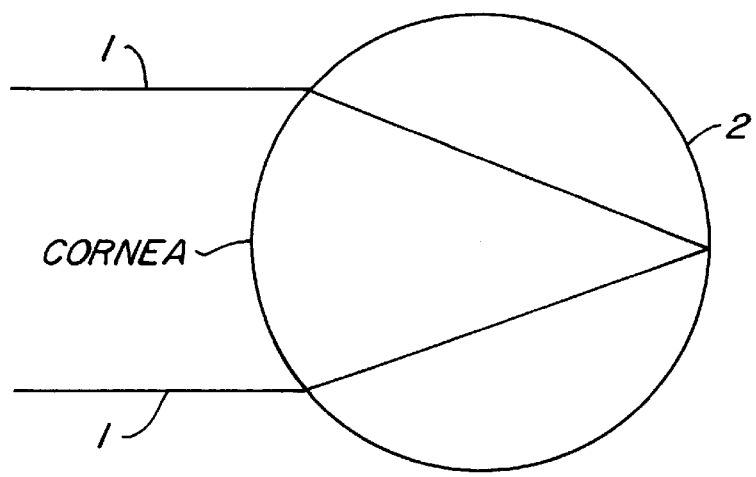
FIG. 1.
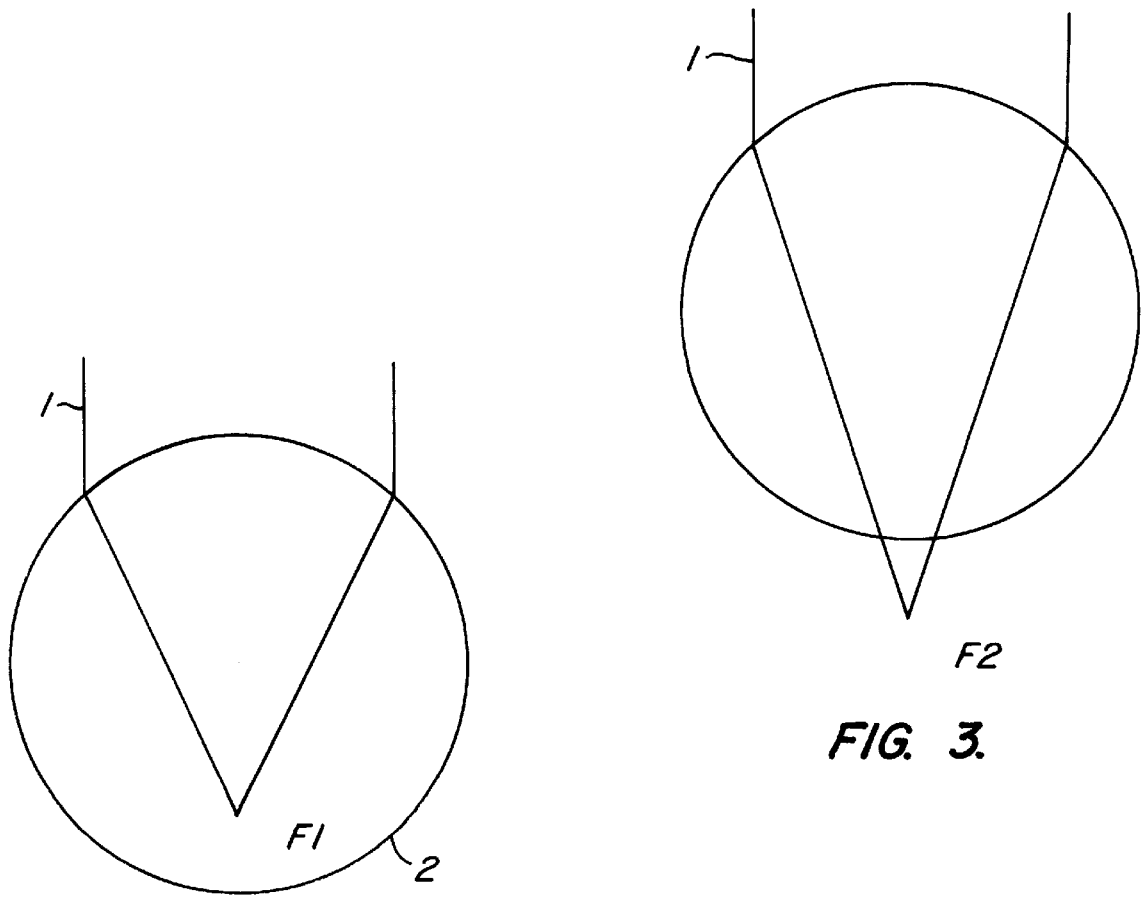
FIG. 2.
FIG. 3.

METHOD AND APPARATUS FOR ADJUSTING CORNEAL CURVATURE USING A FLUID-FILLED CORNEAL RING

CROSS-REFERENCE TO RELATED APPLICATIONS

This application is a continuation-in-part of U.S. patent application Ser. No. 08/761,362, filed Dec. 9, 1996, U.S. Pat. No. 5,733,334.

BACKGROUND OF THE INVENTION

This invention relates to a method and apparatus for adjusting corneal curvature and, more particularly, to an implantable device adapted for insertion into the cornea of an eye and which may be modified in the amount of volume it displaces at the time of insertion and at post-operative times to correct refractive error by adjusting or removing solid material from the implanted device or augmenting said device with solid material.

Ametropia, an undesirable refractive condition of the eye, has three main subdivisions: myopia, hyperopia, and astigmatism. In myopia, by far the most common type of ametropia, the parallel light rays 20 which enter the eye as shown in FIG. 1 come to a focus F1 in front of the retina 24 as shown in FIG. 2. In hyperopia, the rays of light 20 come to a focus F2 behind the retina 24 as shown in FIG. 2 When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye which acts to change the light-bending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomileusis which can steepen or flatten the central cornea. Keratomileusis was introduced by Barraquer of Colombia in 1961 and essentially involves grinding a corneal button into an appropriate shape to correct the refractive error and replacing the reshaped corneal button. Some of the more common keratorefractive procedures are discussed below, none of which have currently shown itself to have all the characteristics of an ideal keratorefractive procedure. The disadvantages of corneal refractive surgery include limited predictability, lack of reversibility, corneal destabilization, optical zone fibrosis, post-operative discomfort, and visual symptoms such as glare, halos, and starbursts.

In radial keratotomy (RK) multiple peripheral radially directed incisions are made into the cornea at 90–95% depth in an attempt to flatten the central cornea and thus correct myopia. The problem of unpredictability of result was tackled by multiple extensive retrospective analyses of the patients in whom surgery had already been performed. These studies revealed certain factors that seemed to control the outcome of the surgery, such as the size of the optical zone, the initial keratometric readings, corneal diameter, corneal rigidity, number of incisions, incision depth, intra-ocular pressure, thickness of the cornea, and degree of astigmatism. Age and sex are also factors that are taken into consideration in most of the nomograms which have been devised to predict what effect to expect for a certain surgery. At one point, many experts in the field considered it nearly impossible to fully and accurately correct patients in one surgery and felt that RK should be considered a two-stage surgery, with the initial surgery to achieve the "ball-park" correction, followed by an enhancement procedure to adjust or titrate the result near the desired outcome for an individual eye. It was felt that because of individual variability which may lead to an under or over-correction in the individual different from that predicted by the nomogram, attempting to fully correct the refractive error in one surgery could lead to over-correction in a not insignificant percent of the surgeries, resulting in hyperopia which is much more difficult to correct. Unfortunately, the second-stage surgery is even less predictable than the initial procedure. No one has yet devised a formula to take into account the profound changes which occur in the cornea after the initial RK, especially when weeks or months have passed. Most studies quote only 50–60% of eyes achieving 20/20 or better visual acuity following RK. Patients who are accustomed to 20/20 or better corrected visual acuity before surgery are not typically satisfied with less than 20/25 or 20/30 uncorrected post-operative visual acuity.

In addition, a gradual hyperopic shift is a major concern after RK. Refractive stability is critical for all refractive procedures but all corneal refractive procedures show significant degrees of instability. To date, there has been no clear explanation of why the cornea is destabilized by RK. A recent report on the long-term results of RK stressed the "natural" hyperopic refractive progression of "normal" eyes as a function of age. It is possible that patients are initially over corrected and the over-correction masked by the patient's accommodative powers. With time and loss of accommodation, the hyperopia may be gradually unmasked with the hyperopia becoming visually symptomatic. At the time of surgery, a patient may be corrected with resultant slight hyperopia and yet have 20/20 vision because of the ability of the lens to accommodate. There is a range of residual correction within which the patient can have 20/20 uncorrected vision. This range varies depending on the individual but probably spans two to three diopters. Even with this range, the percentage achieving 20/20 is only 50–60%. This reflects poorly on the precision of the technique. It is important to note that this range diminishes with presbyopia, or loss of accommodation which usually begins at about 45 years of age. This results in the percentage achieving 20/20 dropping from the 50–60% described above. It is obvious that RK does not qualify as a simple, safe, predictable procedure to adjust the refractive outcome after the initial RK has been performed. Most ideas to contend with the corneal shape after this event have been purely empirical. Thus an easy method to fine-tune a refractive correction that is minimally invasive and easily performed, would require serious consideration.

Laser stromal ablation procedures, such as photorefractive keratectomy (PRK) for correction of refractive disorders are currently popular and have had reasonable success. These procedures are not, however, spared from the problem of unpredictability. Essentially, in the treatment of myopia, laser energy is imparted to the central cornea thereby causing excision of more tissue centrally and a resultant flattening of the cornea. Unfortunately, the final refractive effect is determined not only by the amount of ablation but also by the healing response to the keratectomy. The cornea actively lays down new collagen and the epithelium undergoes a hyperplastic response, among other responses, in an attempt to repair the damage to its surface. This causes regression, or a shift backwards towards myopia, which can gradually occur over a period of months to years. An undesired effect of new collagen deposition is stromal scar formation which manifests as stromal haze and possible decrease in contrast sensitivity by the patient. This corneal stromal opacification is variously referred to as fibrosis, scarring, or haze which is associated with reduced visual acuity and contrast sensitivity, regression of the refractive effect, and poor night vision. Predictability with PRK is an issue, as with RK. Most published results of outcome after PRK treatment for myopia show 80–94% of eyes obtaining uncorrected visual acuity of 20/40 or better while the percentage of patients achieving 20/20 is significantly less. These numbers are in spite of the fact that there is a range of residual refraction at which the patient can still see 20/20 as previously explained. It can be assumed that a significant proportion of those achieving 20/20 after PRK are actually slightly hyperopic. It may very well be that with time, a significant percentage of those patients develop "progressive hyperopia", or an unmasking of the latent hyperopia. So, although the percentage of patients achieving 20/20 after PRK is not acceptable by the definition of an ideal refractive procedure, it may be inflated as was the initial results with RK. Although visual recovery is slow in RK, it is quicker than after PRK. A second laser ablation procedure is usually undertaken with caution since it may cause a greater healing response with even more regression than the initial procedure. Again, as in RK, the laser ablation procedure is not completely predictable, partly because one cannot predict an individual's wound healing response.

For years it has been thought that refractive surgery with intracorneal implants could be used in the correction of ametropia. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses included surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention.

Zhivotosvskii, D. S., USSR Patent No. 3887846, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the ring are not described.

A. B. Reynolds (U.S. Pat. No. 4,452,235) describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia:

1. The first problem is concerned with the ability to predetermine the shape and size of a implant that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.

2. The refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area,—the inherent individual variability, in that while the outcome may be stable, it may very well be an inadequate refractive outcome that is stable.

Another unaddressed issue is that even with the implant, surgeons will aim for a slight under-correction of myopia because, in general, patients are more unhappy with an over-correction that results in hyperopia. Again, the refractive outcome may be more stable than in RK or PRK but it may be an insufficient refractive result that is stable.

Simon (U.S. Pat. No. 5,090,955) describes a surgical technique that allows for modification of the corneal curvature by inter-lamellar injection of a synthetic gel at the corneal periphery while sparing the optical zone and intraoperative removal of such gel to decrease the volume displaced and thus adjust the final curvature of the central corneal region.

Siepser (U.S. Pat. No. 4,976,719) describes another ring-type device to either flatten or steepen the curvature of the cornea by using a retainer ring composed of a single surgical wire creating a ring of forces which are selectively adjustable to thereby permit selective change of the curvature of the cornea, the adjustable means comprising a turnbuckle attached to the wire.

There are several mechanisms by which peripheral manipulation of the cornea affects anterior corneal curvature. The cornea, like most soft tissues, is nonlinear, viscoelastic, nonhomogeneous, and can exhibit large strains under physiologic conditions. The whole eye is geometrically extremely complex and the biomechanics technique capable of systematically modeling this reality is the finite element method which assumes small strains (a measure of deformity), homogeneity, and linear elastic behavior. Two simple mechanisms will be briefly described.

A simple example is helpful in understanding the first mechanism. Assume a loose rope R between two fixed points P1 and P2 as in FIG. 4a, which forms a curve, the lowest point P being in the middle. Referring to FIG. 4b, a weight w placed on the rope between the middle point P and one fixed point will cause the central portion of the rope to straighten. The cornea C demonstrated in FIG. 5(a) and FIG. 5(b) behaves similarly, the two fixed points, P1 and P2, analogous to the limbus of the eye and the weight W similar to the intrastromal implant 30 which, when inserted in the cornea in surrounding relation to the corneal central optical zone, causes the corneal collagen fibers to deviate upwards at (21) above the implant, and downwards at (22) below the implant. In essence, this deviation of the cornea around the peripheral implant caused by volume displacement in the peripheral cornea results in other areas of the cornea losing "slack", or relatively straightening as shown at (23).

Mechanical expansion of the implant diameter as shown by expansion of the implant 30 in FIG. 6(b) as compared to FIG. 6(a) also flattens the central corneal curvature whereas constriction of the implant 30 steepens the central corneal curvature, analogous to the two fixed points in the example, FIG. 4(a) and FIG. 4(b), being moved together and causing the rope in the middle to sag more. This is permitted to occur, in part, because the boundary nodes at the limbus are not completely fixed. In summary, there is a micro-deviation caused by the bulk of the implant 30 itself within the peripheral tissue, slightly flattening the central curvature of the cornea, and a constricting or expanding implant altering the fixed points and thus altering corneal curvature. A constricting or expanding implant is likely to cause a less stable refractive outcome because the inward or outward forces of the implant against the corneal stroma may gradually cause further lamellar dissection and dissipation of the forces. A more consistent outcome is likely to be achieved with varying the volume displaced in the peripheral cornea as described by Simon.

The second mechanism is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called 'keratomileusis' and those involving addition received the name of 'keratophakia'. Intrastromal corneal ring add bulk to the periphery and increasing the thickness of the ring results in a more pronounced effect on flattening of the anterior corneal curvature by "increasing (thickness) in its periphery".

The ideal keratorefractive procedure allows all the advantages of eyeglasses or contact lenses, namely, being able to correct a wide range of refractive errors, accuracy or predictability, allowing reversibility in the event that the refractive state of the eye changes and it becomes necessary to adjust the correction again, yielding minimal complications, and associated with technical simplicity, low cost, and being aesthetically acceptable to the patient. The goal of refractive surgeons should be to achieve 20/20 uncorrected visual acuity with long-term stability in greater than 95% of patients. None of the currently available refractive surgery procedures generate this degree of accuracy or stability.

Once again, an easy procedure to post-operatively fine-tune the refractive correction and corneal curvature which is often influenced by changes in corneal hydration status, wound healing responses, and other unknown factors, is not available. Each of the techniques described suffers from a limited degree of precision. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

SUMMARY OF THE INVENTION

An adjustable intrastromal device adapted for implantation in the cornea and formed of a flexible hollow shell composed of a material such as a silicone or urethane polymer, with a chamber that may be filled with a biocompatible material such as saline or gel. Preferably, the device has more than one compartment, each of which is watertight and distinct from the other compartments. Each compartment contains a predetermined amount of the biocompatible fluid described, and the device is implanted in the cornea in surrounding relation to the optical zone of the cornea. Increased volume displaced by the ring results in greater flattening of the central anterior corneal curvature thus correcting myopia. Preferably, the myopia is slightly overcorrected resulting in more flattening of the cornea than necessary for optimal vision. The corneal curvature is then adjusted after implantation of the device into the cornea by selectively removing the fluid from a specific compartment, thus decreasing the volume of the implant in a discrete fashion and resulting in steepening the corneal curvature and producing a myopic shift.

The implant is easily adjustable on multiple occasions following the initial surgery of implantation and thus allows for adjustment of the refractive outcome at a later date without necessitating the removal of the implanted device.

DESCRIPTION OF THE DRAWINGS

FIG. 1 is a schematic representation of a horizontal section of the human eye;

FIG. 2 is a schematic representation showing how the light rays focus in front of the retina of the eye in the condition of myopia;

FIG. 3 is a schematic representation showing how light rays focus behind the retina of the eye in the condition of hyperopia;

DETAILED DESCRIPTION OF THE INVENTION

Figure 4A:
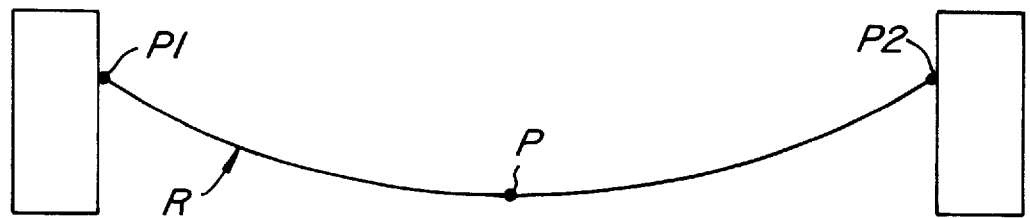
FIG. 4(a) is a schematic of a rope suspended at its ends between two fixed points provided for the purpose of illustrating an underlying concept of the operation of corneal rings.
Figure 4B:
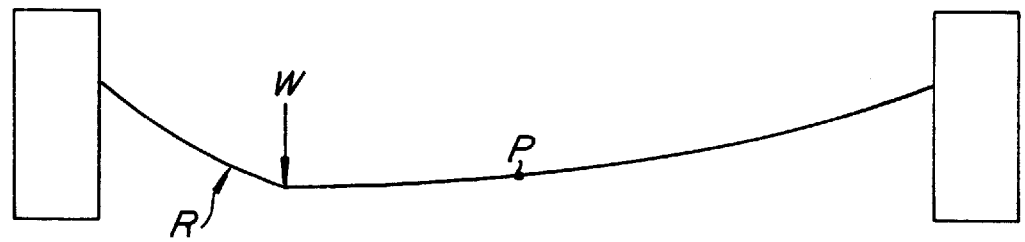
FIG. 4(b) is a schematic illustration which shows the rope in FIG. 4(a) with the force of a weight applied to the rope between its midpoint and one of the fixed points.
Figure 5A:
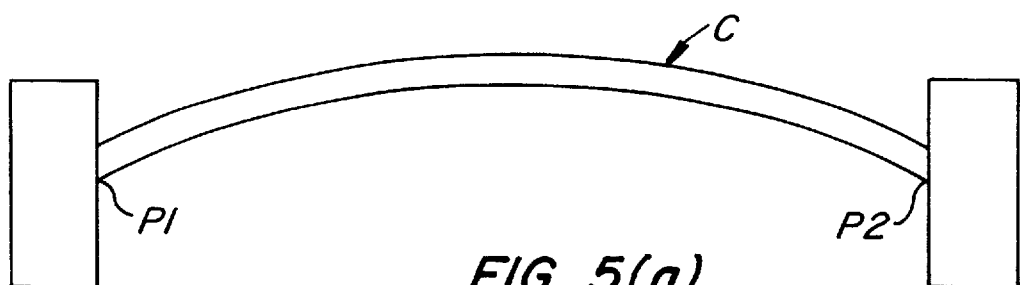
FIG. 5(a) is a schematic illustration showing the cornea of an eye wherein the cornea is fixedly attached at diametrically opposed points on the surrounding limbus.
Figure 5B:
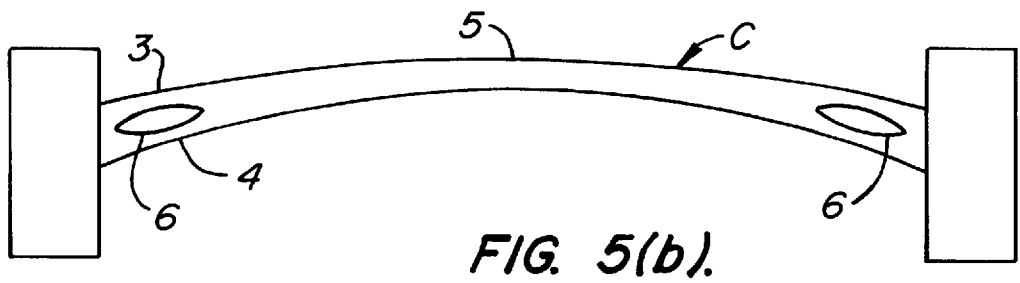
FIG. 5(b) is an illustration similar to FIG. 5(a) but showing the curvature effects produced on the cornea because of the presence of an intrastromal support implant in the cornea.
Figure 6A:
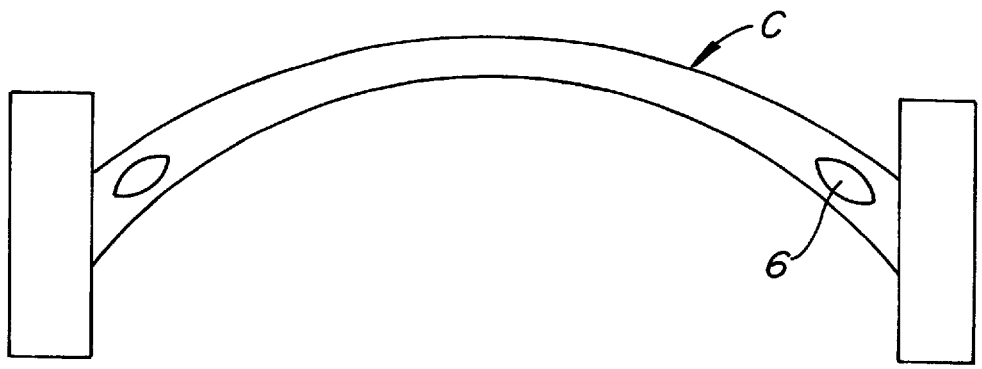
FIGS. 6(a) and 6(b) are cross sectional schematic views of a cornea for showing the effect produced by an expansion of the adjustable implant of the invention after its implantation in the cornea.
Figure 6B:
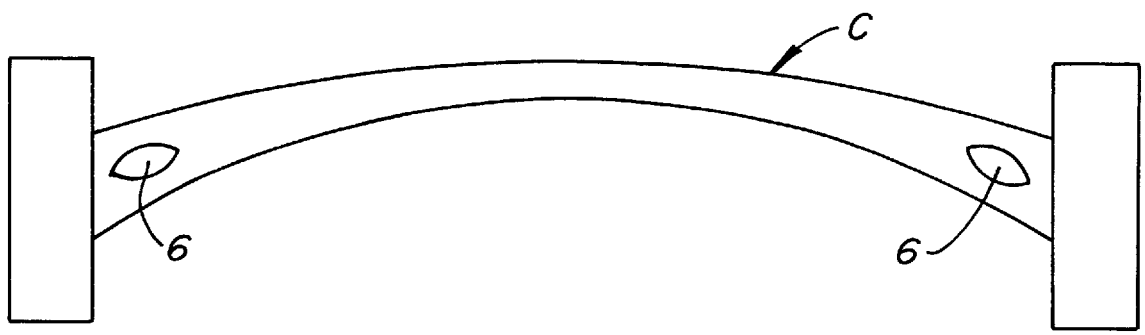
Figure 7A:
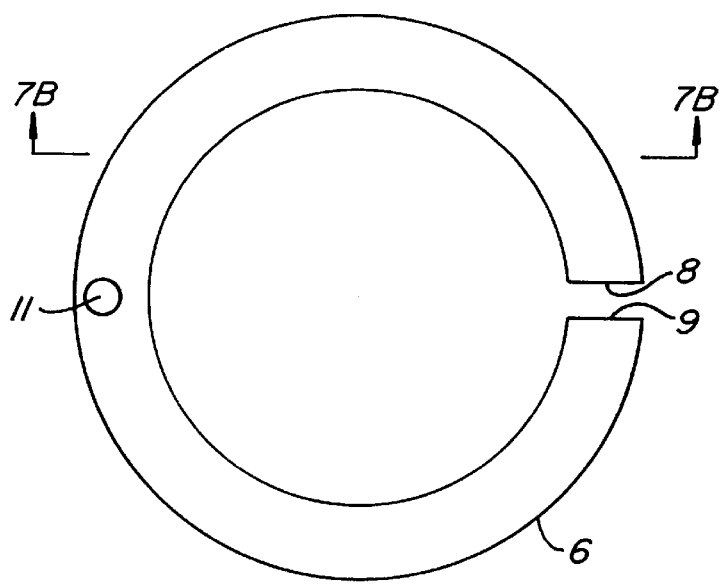
FIG. 7(a) is a plan view of the flexible device of the invention wherein the device has been severed by a radial cut.

Referring more particularly to the drawings, there is shown in FIG. 7(a) an embodiment of the invention which comprises an adjustable, split-ring, multi-lumen implant. The implant forms an enclosure for receiving a filler such as saline which is easily removable. The biocompatible fluid filler is preferably normal saline or sterile water but any other biocompatible and acceptable filler such as hyaluronic acid, hydrogel solutions or dextran might be equally acceptable as a liquid filler. The implant has one or more compartments as shown in FIG. 8, each of which is water-tight and distinct. Each compartment is filled with a biocompatible fluid. The compartments may extend along the length of the ring or may only partly extend along the length of the ring. The cross section of the ring may be of various geometric shapes including circular, oval, rectangular, square, or triangular. The diameter of the cross section of each compartment may vary along its length.

Figure 9A:
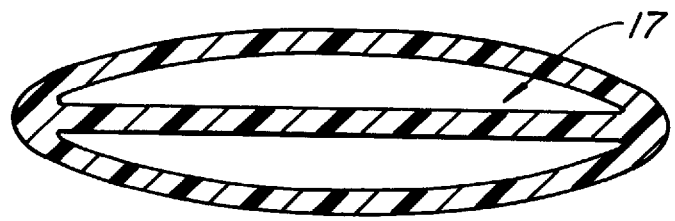
FIG. 9A is a cross section view of an embodiment of the ring with chambers that are horizontally divided.
Figure 9B:
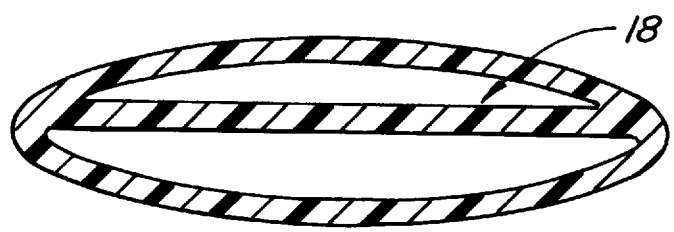
FIG. 9B is a cross section view of the ring from FIG. 9A in which the superior chamber has been punctured.

The implant 6 comprises a tubular shell 7 made of an elastic material, such as a silicone, acrylic or urethane polymer and in FIG. 7(a) is shown as a split ring implant. The shell material has adequate stiffness such that the implant will maintain its generally circular shape in plan view when sufficiently filled and also have adequate resiliency to allow an increase in thickness with filling, and flattening with removal of the filler material as shown in FIG. 9. The shell must have sufficient structural integrity, strength, elasticity and elongation ability to generally maintain its circular shape and be expandable. Its composition material may be similar to that used in producing foldable or deformable intraocular lenses such as a silicone polymer, urethane polymer, acrylic polymer, or that material used in soft contact lenses. If the compartment is made to be removed from the ring, the compartment wall should have similar material properties to that described for the overall ring wall.

Figure 7B:
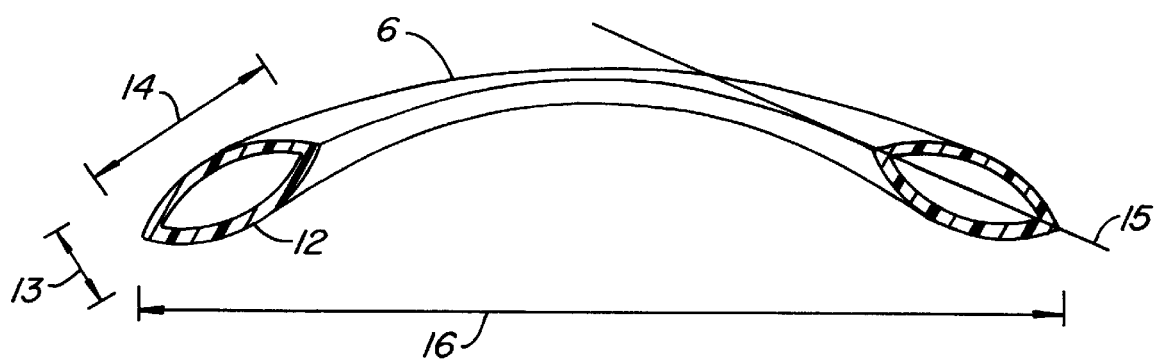
FIG. 7(b) is an enlarged diametral cross section view as taken along the section line 7B—7B in FIG. 7(a)
Figure 8A:
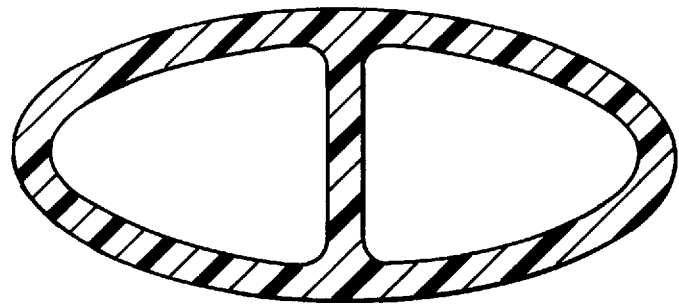
FIG. 8A is a cross section view of a ring of the invention with chambers that are vertically divided.
Figure 8B:
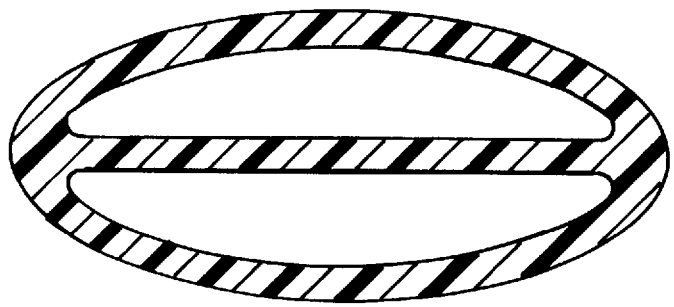
FIG. 8B is a cross section view of a ring of the invention with chambers that are horizontally divided.
Figure 8C:
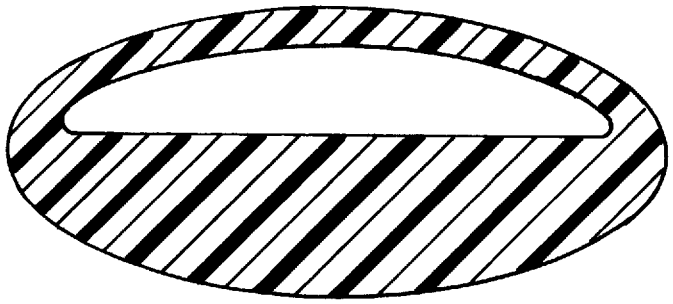
FIG. 8C is a cross section view of an embodiment of the ring with a reinforced inferior wall.
Figure 8D:
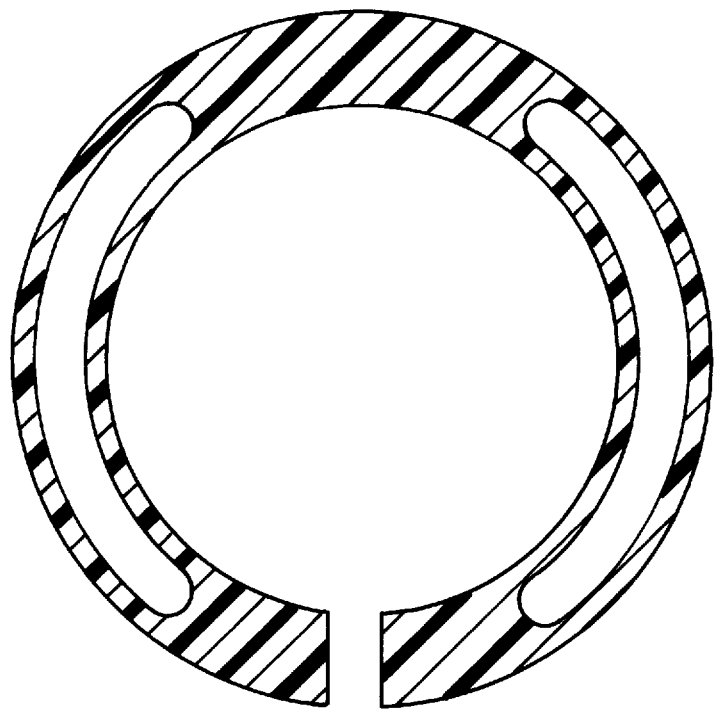
FIG. 8D is a plane view of the ring showing two chambers that do not extend completely around the ring.
Figure 8E:
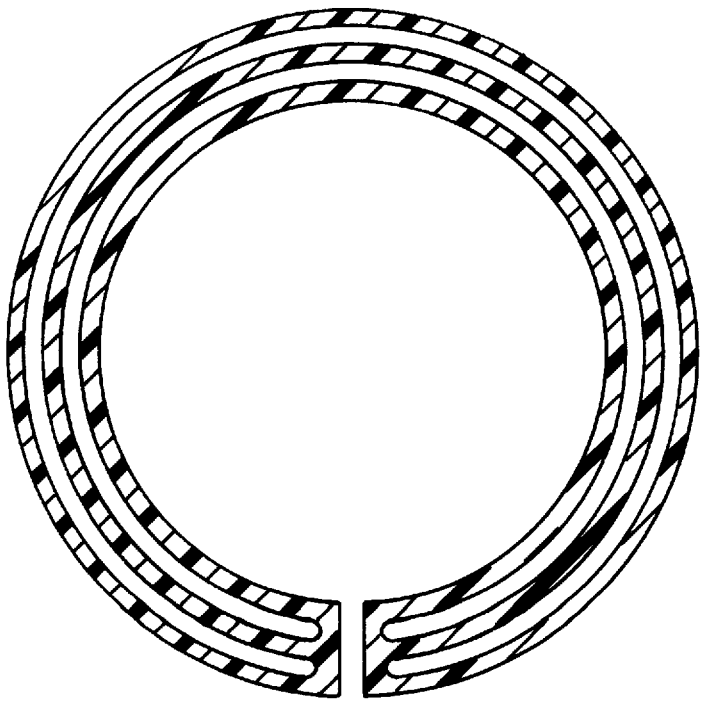
FIG. 8E is a plane view of the ring showing two chambers that both extend completely around the ring.

The cross section of the implant 6 as taken in a radial plane through the center of the implant is elliptically shaped as seen in the section view demonstrated in FIG. 7(b). The different embodiments shown in FIG. 13 can each be modified to provide a number of subembodiments by altering variables such as the composition material of the implant wall, manner of implant connection, type of biocompatible filler material, and cross-sectional surface parameters of the implant, e.g., forming the implant from cross sections in the form of a circle, square, rectangle, triangle, oval, etc. The major axis 15 of a transverse cross section of the implant 6 is such that it corresponds to the slope of the corneal arc of the anterior pole of the cornea, thus forming the conic section. This angle is approximately 20 to 25 degrees as shown in FIG. 7(b). The two ends 8, 9 of the split implant are squared off so that they may juxtapose each other as shown in FIG. 7(a) and may be fixably joined at the time of surgery by such methods as suturing or gluing.

The device is adapted to be implanted into the peripheral stromal cornea. It is of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea intrastromally and consists of an elastic material which is biocompatible, and more specifically, compatible with ocular tissues. It is comprised of a hollow implant of thickness and circumference both of which are variable such that the central optic zone is flattened by removing fluid from a selected compartment. The dimensions as shown in FIG. 7(b) include a maximal thickness (55) (after complete augmentation) of 0.1–.80 mm, width (14) of 0.5 to 1.5 mm and an outer over-all diameter (16) of 6–10 mm. The thickness of the shell 7 of this implant 6 may be varied as shown in the subparts of FIG. 13.

Figure 11A:
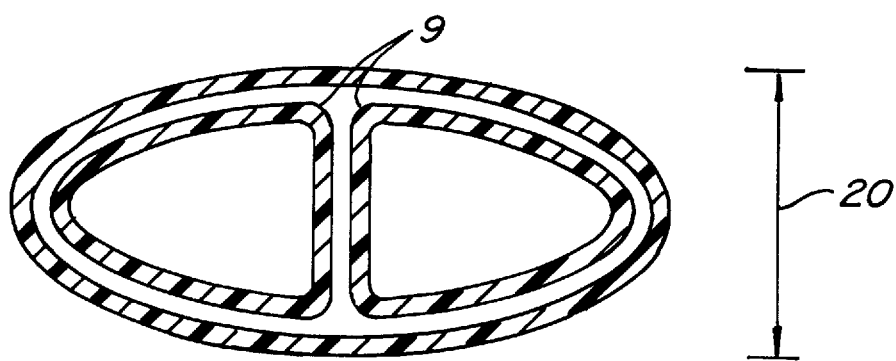
FIG. 11A is a cross section view of an embodiment of the ring containing two inflated chambers, both of which are separable from the outer shell of the ring.
Figure 11B:
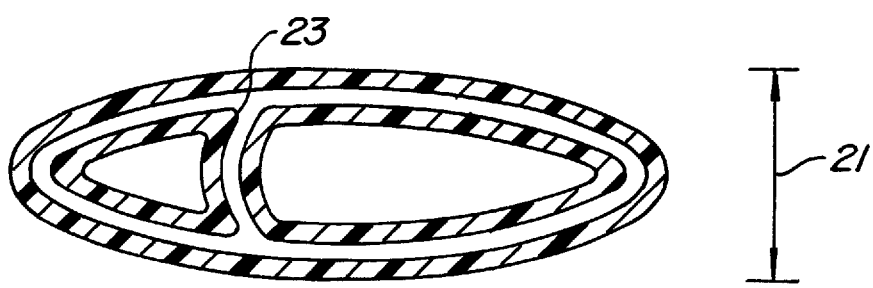
FIG. 11B is a cross section view of the ring from FIG. 11A after one chamber has been punctured, showing decrease in thickness of the ring.
Figure 11C:
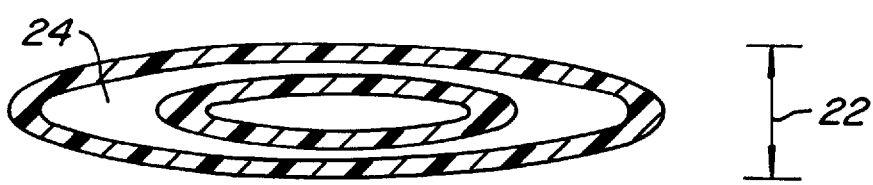
FIG. 11C is a cross section view of the ring from FIG. 11B after the punctured chamber has been removed from the implanted ring, showing a further decrease in thickness of the ring.

The implant may contain only one or multiple chambers, each water-tight and distinct from the other compartments. The compartments are each water-tight but the wall of the compartment may or may not be an integral part of the outer wall of the ring. If the compartment wall is separate from the shell wall as demonstrated in FIG. 11, it permits the added advantage of allowing not only fluid removal from the compartment thus decreasing overall ring thickness, but also permits removal of the compartment itself from the ring, thus allowing a further decrease in overall ring volume as demonstrated in FIGS. 11a to 11c. The thickness 22 of the ring in FIG. 11c is less than the thickness 21 of the ring in FIG. 11b, which in turn has a smaller thickness than the ring in FIG. 11a. Each compartment is thus a distinctive unit. These adjustments are performed with the ring implanted in the cornea. There may be several compartments, distinct from the outer wall, present within the lumen defined by the shell of the ring. These compartments may vary in size and shape and may extend 360 degrees but not necessarily so, especially in situations requiring a differential ring thickness such as astigmatism.

Figure 12A:
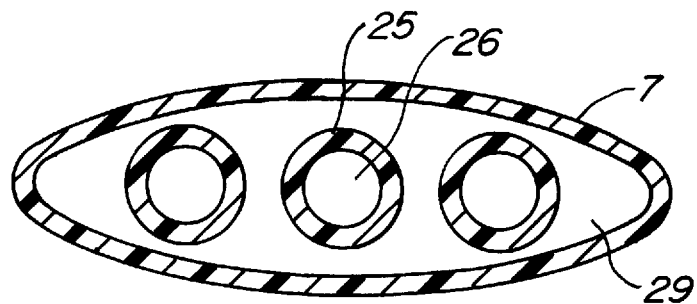
FIG. 12A is a cross section view of an embodiment of the ring showing three microcapsules which contain fluid.
Figure 12B:
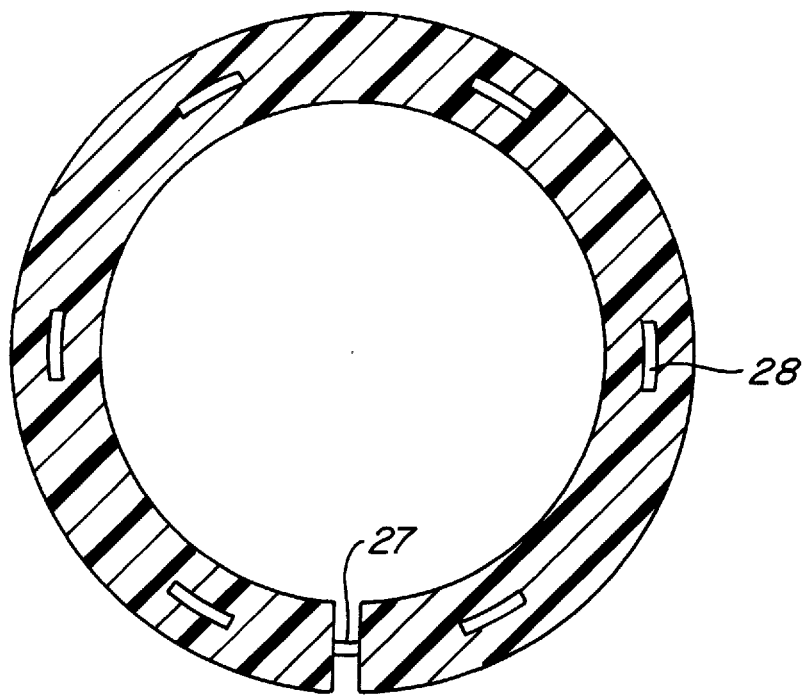
FIG. 12B is a plan view of the ring showing holes or perforations in the wall of the ring and two openings at the split area of the ring.

In yet another subembodiment demonstrating the possible variations of an implant with an outer wall and inner compartments, each of which are a distinctive unit, the outer wall of the ring encloses a number of individual microcapsules or beads 25 which contain closed volumes of fluid 26 as shown in FIG. 12. Each of the small volumes are hermetically delimited by a thin membrane and filled with a biocompatible liquid. The outer wall has openings 27, 28 which provide fluid communication between the outside of the ring and the lumen 29 containing the microcapsules. Each microcapsule may be separately pierced with a sharp instrument or with a laser allowing fluid to leak out of the capsule through the outer wall openings and to eventually be absorbed by corneal tissue. This results in ring thickness decreasing, thus steepening corneal curvature and allowing a fine-tuning adjustment of the refractive outcome. The advantage would be that although a biocompatible material is being removed from the ring, no material is directly removed from the ring out of the cornea. This technique fulfills a need to provide an opportunity to modify the corneal curvature by adjusting the volume of the implant, at will, with very mial surgical intervention. The use of microcapsules is well-known in the pharmaceutical field. It is also well-known that fluid injection into a healthy cornea is rapidly resorbed. Fluid injection into the stroma of the cornea is commonly practiced following cataract surgery to facilitate corneal wound self-sealing.

If the walls of the compartments are distinct from the outer wall as in FIG. 11, then the outer wall may be composed of a biocompatible, porous material such as that used in hemodialysis tubes. The characteristics of the porous shell are similar to that already described including sufficient flexibility to allow the thickness of the device to decrease when the biocompatible filler material is removed. Advantages of a porous shell include improved nutrient diffusion to the anterior corneal stroma. Another method to allow improved nutrient diffusion to the anterior corneal stroma is to place openings 28 or fenestrations in the shell of the implant. The openings may be multiple, radially or longitudinally oriented, of variable length and width and situated on the anterior or posterior surface of the device.

Depending on the amount of refractive error, an appropriate embodiment varied in shape, size, circumference, strand size, type of biocompatible filler material, number of compartments present are chosen. The elastic shell 7 can also be varied as shown by the embodiments of implant illustrated in FIGS. 13(a)–13(d). The choices include:

1. The absence of supporting polymethylmethacrylate (PMMA).

Figure 13A:
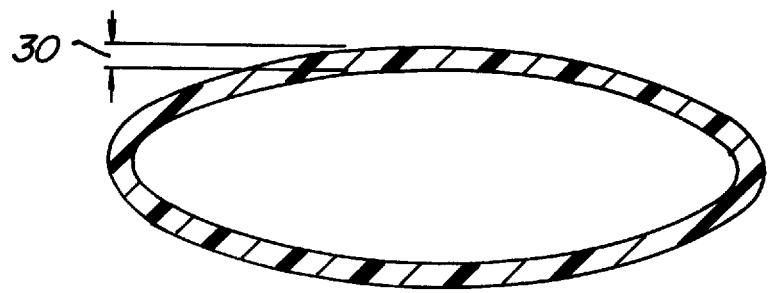
FIGS. 13A through 13D are radial cross section views of modified forms of the ring of the invention.
Figure 13B:
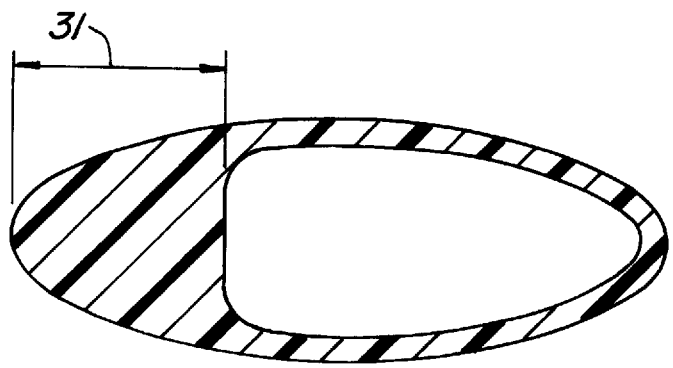
Figure 13C:
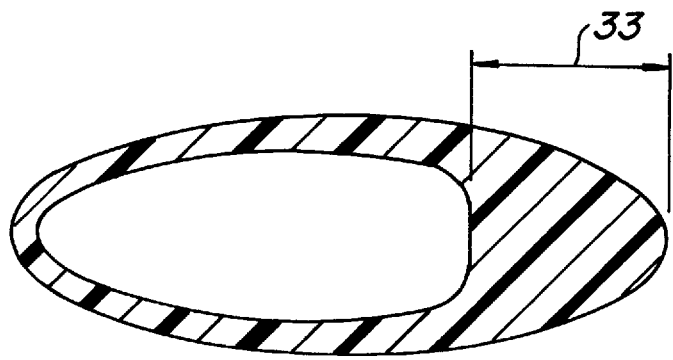
Figure 13D:
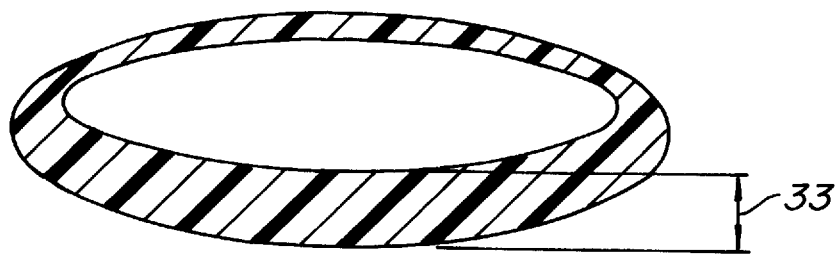
Figure 13E:
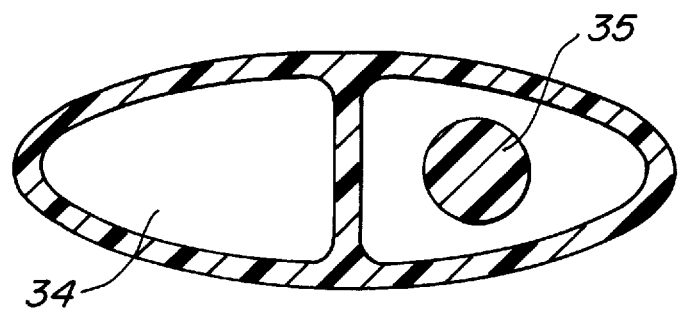
FIG. 13E shows a cross section of the ring with a combination of a fluid chamber and the presence of a strand material.

2. PMMA or other stiff physiologically acceptable polymer backbone reinforcing the inner circumference of the implant wall as shown in FIG. 13(c). The thickened area 32 shown in FIG. 13(c) may be increased thickness of the elastic material composing the walls or it may be PMMA.

3. PMMA or other stiff polymer backbone reinforcing the outer circumference of the implant wall as shown in FIG. 10(b).

4. Support of both inner and outer circumferences.

5. A compartment ring used in combination with the presence of other biocompatible solid filler material that may also be removed. The compartment 34 in FIG. 13(e) contains fluid and the same ring also contains a solid strand-like filament 35 that may also be removed.

The size of the device chosen should be such that the range of over-correction or under-correction secondary to individual variability of response to surgery may be comfortably corrected (not requiring removal of the entire ring) by the methods described. The maximal thickness, circumference, and type of supporting backbone is chosen prior to insertion of the implant. The ideal embodiment, given the preoperative refractive state and other pertinent data, is chosen prior to operating and then that embodiment further manipulated as necessary to determine the ideal curvature. The device is inserted into the peripheral cornea at an adequate depth and then further adjusted in order to more precisely adjust the shape of the cornea and focus the light entering the eye on the retina. The intra-operative keratoscope or automatic keratometer may be helpful. However, intra-operative curvature measurements in surgeries involving the cornea have not been shown to be predictably reproducible.

The device is implanted into a circular lamellar channel formed at ½ to ⅔ corneal depth with a circular dissecting instrument that requires only a small midperipheral corneal incision. A knife is used to make an approximately 2 mm radial incision beginning at 2.5 to 3.5 mm from the corneal center. The surface of the cornea is cut only at this incision. A Suarez spreader is introduced into the bottom of the incision and a small lamellar channel created. Application of a vacuum centering guide is used to fix the globe while an 8–9 mm outer diameter lamellar channeling tool introduced through the incision into the lamellar channel is rotated to produce a 360 degree channel around the corneal midperiphery at ½ to ⅔ corneal depth. After the channeling tool is removed, a circular endoscopic-type forceps is inserted into the same channel and rotated 360 degrees such that the forcep tip emerges from the radial incision. One end of the device is inserted into the forceps, the forcep jaws closed thus gripping the device, the circular forceps rotated until the device is progressively pulled into place. The head and tail of the device are brought together and may be fixed together with suture or glue.

In summary, adjustment or choice of implant size, shape, width, shell thickness, and circumference, factors affecting the corneal curvature and refractive outcome, occurs in three distinct temporal stages:

1. Preoperatively, the above mentioned variables and presence or absence of a supporting backbone are chosen using nomograms developed from retrospective studies as a guide to the selection of each variable.

2. Intraoperatively, the implant tightness is adjusted as necessary, aided by the use of the intraoperative keratoscope if necessary.

Figure 14A:
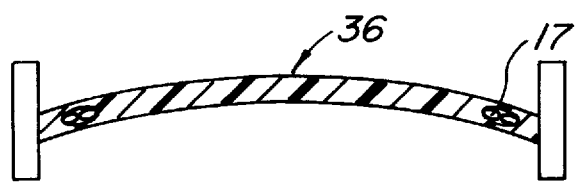
FIGS. 14A and 14B show cross-sectional views of the cornea and ring before and after the chambers have been punctured.
Figure 14B:
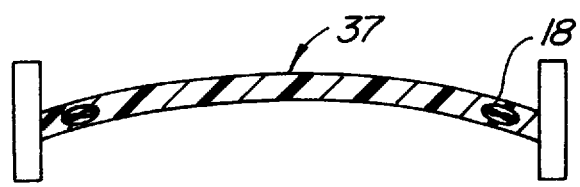
Figure 15A:
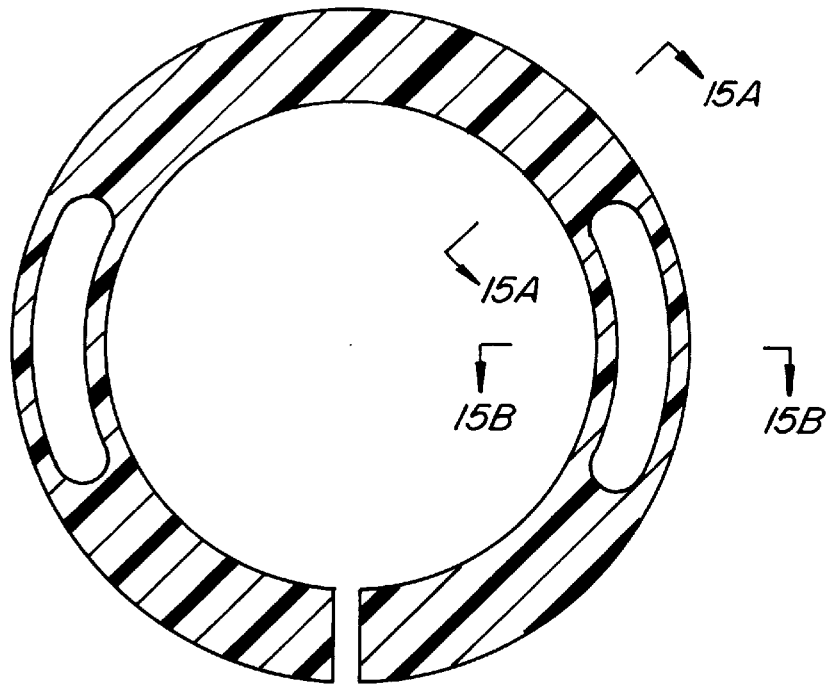
FIG. 15A is a plan view of another embodiment of the ring and showing the locations of isolated compartments therein.
Figure 15B:
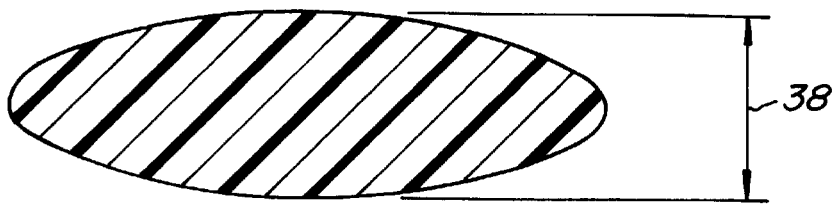
FIG. 15B is a cross section view of the ring in FIG. 15A as taken along the section line 15A—15A.
Figure 15C:
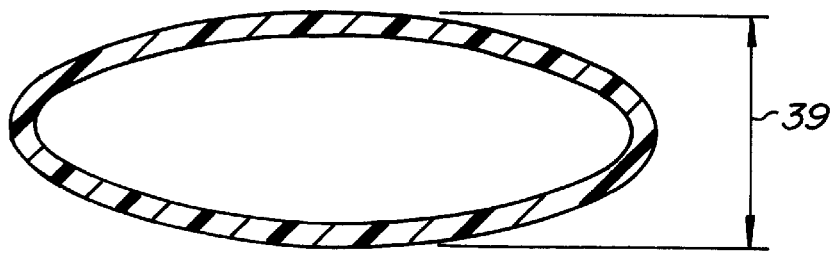
FIG. 15C is a cross section view of the ring in FIG. 15A as taken along the section line 15B—15B and showing a relatively thin wall.
Figure 15D:
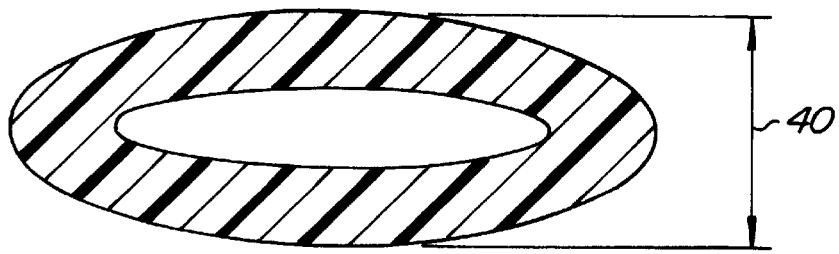
FIG. 15D is a cross section view of the ring in FIG. 15A as taken along the section line 15b—15b and showing a relatively thicker wall compared to the ring section in FIG. 15C.

3. Post-operative adjustments. Simple, easily performed postoperative adjustments, which avoid the complications of reoperation concomitant with most keratorefractive procedures, are rendered feasible by this mechanism of adjustment. This postoperative adjustment can compensate for an inadequate preoperative implant choice, for corneal hydration intra-operatively which results in a different corneal curvature after corneal hydration status changes postoperatively, for an unexpected or variable wound healing response in the periphery to the implant, and for later refractive changes caused by unknown factors. This postoperative adjustment is made possible by an elastic corneal implant containing multiple compartments filled with fluid and distinct from the other compartments, one or more compartments from which the fluid can be removed thus decreasing the thickness of the implant and resulting in increasing corneal curvature. Removal of fluid by selective compartment puncture minimally disturbs the stroma-implant interface compared to removing the implant itself, thus minimizing the effects wound healing and edema will have on the adjustment. This postoperative adjustment appears to be a necessary adjunct to any method that seeks to meet the criteria for the ideal keratorefractive procedure. If the refractive outcome is not ideal, these are the steps that may be taken:

a. Corneal curvature may be flattened by the following method. A strand of biocompatible material within the implant may be attached to a larger diameter strand such that as the strand within the implant is removed, the larger strand is progressively pulled into place thus thickening the implant and flattening the anterior corneal curvature.

b. As shown in FIGS. 14(*a*) and 14(*b*), if the corneal curvature 36 is too flat after surgery (FIG. 14*a*), ring thickness is decreased by selectively puncturing a compartment 17 allowing fluid to leak out, or the fluid may be removed with a syringe and needle. The compartment is now collapsed 18 and the corneal curvature 37 is steepened. There is no attempt to repair the puncture site since the other chambers are distinct and will not leak. More than one compartment may be punctured as necessary. When correcting myopia, a hyperopic outcome is very difficult to correct with any of the current kerato-refractive procedures and overcorrection of myopia does occur. With this device, a hyperopic outcome is relatively easily reversed by fluid removal through selective puncture of one or more compartments. Simple deflation of the ring by fluid removal from one or more compartments results in decreased ring thickness in definable increments, thus allowing fine-tuning of the refractive outcome. Controlled removal of fluid from a ring with a port would be technically difficult because of the extremely small volumes of fluid. This last point requires further elaboration. A similar fluid filled ring has been described by Silvestrini in U.S. Pat. No. 5,466,260. He describes an inflatable ring which can be inflated with saline by the injection of fluid into the ring via a nozzle which is preferably a one-way valve. He also discusses the possibility of fluid extraction by inserting a hypodermic needle into the valve opening and vacuuming fluid from the interior of the ring. However, after implantation of this ring into the cornea, the nozzle is no longer accessible.

A multiple-chamber fluid filled ring overcomes several problems associated with Silvestrini's ring. The manufacture of a minute nozzle or valve which acts as a one-way valve is extremely difficult. Leakage or loss of fluid via the nozzle or valve over the long-term is a significant drawback, since the thickness of the ring decreases with a change in refractive result with fluid loss from the ring. There is also a significant technical difficulty of directing the hypodermic needle into the port and maintaining that position as fluid is being withdrawn. A ring is typically 0.3 mm thick. As the needle attempts to enter the port, the anterior portion of the ring will necessarily give causing compression in that region resulting in thickness decreasing to less than 0.2 mm. The more water-tight the nozzle seal, the more resistance there will be to the needle penetrating the port with a concomitant increase in compression, decrease in ring thickness and much increased risk of perforating the ring wall directly beneath the nozzle. Also, leakage of significant amounts of fluid during puncture of the nozzle with a hypodermic needle to inject or remove fluid may take precise removal of fluid difficult. In addition, the amount of fluid that needs to be removed to effect a refractive change of 0.25 to 0.50 diopters is extremely small. A typical amount that would need to be removed to effect such a change is approximately 0.002 milliliters, which does not leave much room for error.

In contrast, the multiple-chamber fluid-filled ring, each of which is a distinct unit, does not require a port with its possible complications of long-term leakage. Also, the difficulty of withdrawing precise amounts of fluid is overcome by puncturing a select compartment which contains a discrete amount of fluid that is absorbed by the corneal tissue. There is no concern of having the puncture area seal since each unit is distinct and water-tight. Needless to say, fluid cannot be injected once the ring is made and each chamber sealed.

Figure 10:
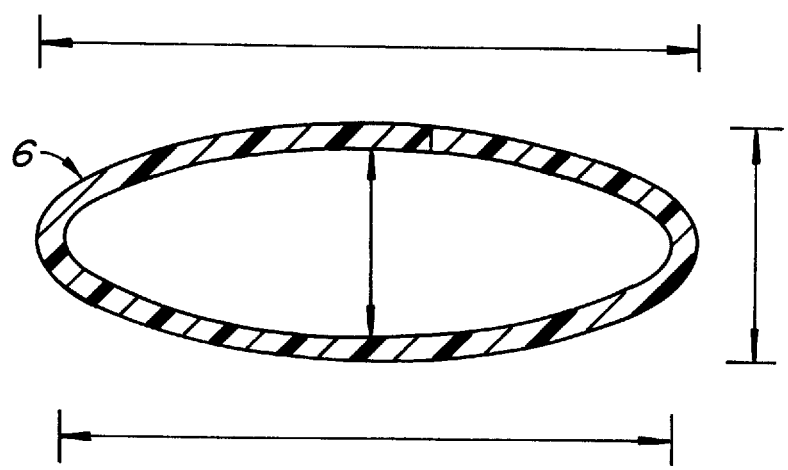
FIG. 10 is a radial cross-section of an embodiment of the ring and showing typical dimensions thereof.

A typical adjustable implant 6 of the invention is shown in FIG. 10. The width of its outer diameter is 0.85 mm, overall thickness is 0.3 mm, and largest inner diameter is 0.75 mm and minor diameter is 0.20 mm. An implant of this size is expected to correct myopia by approximately 3 diopters. Assuming there are three compartments, fluid removal from all three compartments results in flattening of the ring by 0.15 mm or a change in the corneal curvature by 2.0 diopters. The average diopter change for removal of fluid from each compartment is approximately 0.5 diopter. Given an initial myopic patient, the outcome can be overshot by 50% of the initial refraction and the hyperopia still reasonably managed by fluid removal alone.

Overtreatment resulting in hyperopia is a significant disadvantage in most keratorefractive procedures. In radial keratotomy the wound healing processes occur over a period of years and there is often a progressive hyperopia. Patients who become symptomatically hyperopic after surgery are extremely unhappy. Therefore most surgeons use nomograms that attempt to achieve a slight undercorrection.

Concerning photorefractive keratectomy, in one study, it was found the main reason patients did not have their second eye corrected with PRK (given that their first eye was corrected with PRK) was because of dissatisfaction with the hyperopia in their operated eye. This technique easily accommodates post-operative correction of overcorrection hyperopia.

In a simple adaptation of the adjustable implant technique, the device may be used to correct astigmatism.

Curvature variation of the anterior surface of the cornea is responsible for the majority of cases of astigmatism. The light rays converge upon more than one plane and no one principal focus is formed. Astigmatism ordinarily depends on the presence of toroidal instead of spherical curvatures of the refractory surfaces of the eye. It thus becomes obvious that to correct astigmatism certain areas of the cornea must necessarily be corrected to a greater degree than other areas. There may be located in the implant certain size and shape chambers which add dimension to appropriate areas of the ring, relative to the other areas as shown in FIG. 15. Sections of the implant having increased thickness 39 would correspond to the areas of the cornea requiring greater correction. Instead of altering the size or shape of the chambers, the wall of the ring may have a differential thickness 40. A combination of differential wall thickness and variable chamber size may also be used. A combination of a fluid chamber with a solid biocompatible filler material may also be used. Selective puncturing of these chambers modify the outcome in the correction of astigmatism. Variations can occur in the number, length, diameter, volume, and cross-sectional shape of each of the compartments. Variations can occur in the elastic implant which may have a supporting backbone of PMMA or other polymeric material.

It is therefore to be appreciated that by use of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well-suited to adjust a hyperopic refractive outcome; 2) irreversibility of radial keratotomy and laser ablation surgeries; 3) surgical manipulation of the central visual axis with the potential for scar and stromal haze formation following laser ablation procedures; 4) the need for chronic use of steroid drops with its accompanying complications such as cataract and glaucoma; 5) regression with laser ablation procedures, especially following re-operation; 6) reduction of positive sphericity with RK and laser ablation which may result in increased image aberration; 7) the invasiveness of laser in-situ keratomileusis; 8) lack of precision and predictability with all current procedures; and 9) the possible need for repetitive explanting and implanting of intracorneal rings (ICR) in the prior art, which may cause shearing of corneal peripheral channel lamellae with associated variability of effect and also scar formation.

Regarding the last point, methods to adjust implanted ring thickness have been described in the prior art. These methods are only discussed in relation to adjusting the ring thickness during implantation, not post-operatively. Attempts to adjust the thickness of the ring are most useful after corneal curvature has essentially stabilized. Adjustments of devices that have been described in the prior art would necessarily require rotation of the ring with resultant shearing of the corneal ring interface. Rotation of the ring allowing more or less overlap of the individual ring parts thus increasing or decreasing ring thickness is one example. This shearing of the corneal tissue in the immediate vicinity of the ring may alter the corneal curvature in an unpredictable fashion and cause more scarring with unpredictable refractive long-term effects. In the embodiment that is described in this article, the ring thickness is adjusted with only very minimal disturbance of the surrounding tissue. By the nature of the adjustment, there is no rotational movement of the aspect of the ring which is in contact with the corneal tissue with respect to the cornea. To clearly elucidate "rotational movement," it is meant to refer to a rotation of the ring similar to that required for initially inserting the ring into the inter-lamellar channel. With a rotational movement of the implanted ring, the corneal-ring interface is disturbed. In the embodiment described in this article, the corneal-ring interface is essentially undisturbed. Of course, with a decrease in the ring thickness, there will be a minute shift of surrounding tissue. In conclusion, a slight decrease in ring thickness by the adjustment described will not only be much easier to perform, but also have a much more predictable discrete effect.

Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. The various embodiments of the device allows for the fact that individual tissue response to the calculated correction may not be completely predictable, and permits easy adjustments at the time of surgery and more importantly, at a later date after corneal hydration and wound healing responses have been stabilized by simple selective compartment puncture. The nature of these adjustments minimally disturb the implant-corneal interface (unlike the explantation of the ICR) and is thus expected to have a much more predictable effect than even the implantation of the implant itself which causes less of a wound healing response than current procedures such as RK and PRK. In addition, when correcting myopia, a hyperopic outcome is very difficult to correct with any of the current keratorefractive procedures and overcorrection of myopia does occur. According to a presently preferred embodiment of the invention, a hyperopic outcome is relatively easily reversed by suture removal. Typically, in most keratorefractive procedures for myopia, the surgeon aims for a slight undercorrection because of the wish to avoid a hyperopic outcome. The ease with which a hyperopic outcome is adjusted with the implant of the present invention enables the surgeon to aim for full correction, thereby obtaining the full benefit of the nomogram, and resulting in a higher percentage of patients with the desired refractive outcome even without an adjustment of the implant. The surgeon may even choose to slightly overcorrect followed by an adjustment.

It is hypothesized that individual responses to any keratorefractive surgical procedures are variable, that even a "perfect" nomogram will not lead to a reliably predictable result in a particular individual, that a simple, safe, and effective technique for corneal curvature adjustment is desirable and that, preferably, this adjustment should minimally disturb surrounding tissue thus allowing for a predictable effect. This adjustment should also be easily accomplished at some post-operative date after implantation of the implant and after factors affecting corneal curvature changes have stabilized. The implant in its various embodiments may advantageously be adjusted in thickness with ease at the time of implantation and more importantly, on multiple occasions thereafter by simple removal of a discrete amount of biocompatible filler material from the implanted device, thus allowing fine-tuning of the refractive outcome.

In conclusion, in correcting refractive errors with an adjustable implant technique according to a preferred embodiment, an initially inaccurate correction, inadequate adjustment, or even removal of the last strand are easily remedied by removing the implant itself, or better yet, leaving it in place while other refractive procedures, such as laser ablation surgery are considered, if that point is ever reached.

It is also to be appreciated that the foregoing description of the various embodiments of the invention has been presented for purposes of illustration and explanation only and is not intended to limit the invention to the precise form of apparatus and manner of practice described herein. It is to be appreciated therefore, that changes may be made by those skilled in the art without departing from the spirit of the invention as described in the following claims.

I claim:

1. A corneal ring comprising:
    a tubular member to be formed into a ring, the tubular member comprising:
        a biocompatible material; and
        a plurality of internal fluid-filled cavities, each cavity extending along at least a portion of the length of the tubular member.

2. The corneal ring of claim 1 wherein the fluid in at least one of said cavities comprises saline.

3. The corneal ring of claim 1 wherein the fluid in at least one of said cavities comprises a gel.

4. The corneal ring of claim 1 wherein the tubular member comprises a reinforcing backbone extending along at least a portion of the length of the tubular member.

5. A corneal ring comprising:
    a tubular member to be formed into a ring, the tubular member comprising:
        a biocompatible material;
        a cavity extending along at least a portion of the length of the tubular member; and
        a fluid-filled compartment positioned in the cavity and separate from the tubular member.

6. The corneal ring of claim 5 wherein the fluid in the compartment comprises saline.

7. The corneal ring of claim 5 wherein the fluid in the compartment comprises a gel.

8. The corneal ring of claim 5 wherein the compartment comprises a microbead.

9. The corneal ring of claim 5 wherein the compartment comprises a tubular filament extending along at least a portion of the length of the cavity.

10. The corneal ring of claim 5 wherein the cavity includes a strand extending along at least a portion of the cavity.

11. The corneal ring of claim 10 wherein the strand comprises a material selected from the group consisting of polymethylmethacrylate, nylon, mersilene, and polypropelene.

12. The corneal ring of claim 5 wherein the tubular member comprises an opening to provide access to the cavity.

13. The corneal ring of claim 5 wherein the tubular member comprises a reinforcing backbone along at least a portion of the length of the tubular member.

14. The corneal ring of claim 5 wherein the tubular member is porous.

15. The corneal ring of claim 5 wherein the tubular member comprises a plurality of apertures for the exchange of fluids between the cavity and an exterior of the tubular member.

16. A process for adjusting the corneal curvature of an eye, the process comprising the steps of:
    making a radial incision into the cornea;
    at the incision, forming an annular channel between lamellae of the corneal tissue, said channel extending about an optical zone of the cornea;
    inserting into the incision an end of a tubular corneal ring, comprising a tubular member the corneal ring including a plurality of fluid-filled compartments; and
    gradually moving the corneal ring about the annular channel until the corneal ring is fully inserted.

17. The process of claim 16 wherein at least one of said compartments is separate from the tubular member.

18. The process of claim 16 further comprising the step of adjusting a radial cross-sectional area of at least a portion of the corneal ring.

19. The process of claim 18 wherein the adjusting step comprises removing at least some fluid from at least one of said compartments.

20. The process of claim 18 wherein at least one of the compartments extends along a portion of said tubular member and wherein the adjusting step comprises removing fluid from said compartment such that the tubular member has a smaller radial cross-sectional area at said portion.

21. The process of claim 16 further comprising the step of adjusting a thickness of at least a portion of the corneal ring.

22. A process of adjusting the corneal curvature of an eye, the process comprising the steps of:
    in a first operation making a radial incision into the cornea;
    at the incision, formning an annular channel between lamellae of the cornea, said channel extending about an optical zone of the cornea;
    inserting into the incision an end of a tubular corneal ring, the ring including a plurality of internal fluid-filled compartments;
    gradually moving the corneal ring about the annular channel until the ring is fully inserted; and
    in a second operation adjusting a thickness of the ring by removing fluid from at least one of the compartments.

23. The process of claim 22 further comprising the step of adjusting a thickness of at least a portion of the corneal ring in the first operation.

* * * * *